United States Patent
Rivin et al.

(10) Patent No.: US 9,168,144 B2
(45) Date of Patent: Oct. 27, 2015

(54) PROSTHESIS FOR REPLACEMENT OF CARTILAGE

(76) Inventors: Evgeny Rivin, West Bloomfield, MI (US); Allen M. Krass, Troy, MI (US)

(*) Notice: Subject to any disclaimer, the term of this patent is extended or adjusted under 35 U.S.C. 154(b) by 901 days.

(21) Appl. No.: 12/841,463

(22) Filed: Jul. 22, 2010

(65) Prior Publication Data

US 2011/0066243 A1  Mar. 17, 2011

Related U.S. Application Data

(60) Provisional application No. 61/242,152, filed on Sep. 14, 2009.

(51) Int. Cl.
*A61F 2/38* (2006.01)
*A61F 2/30* (2006.01)

(52) U.S. Cl.
CPC ............ *A61F 2/3872* (2013.01); *A61F 2/30965* (2013.01); *A61F 2240/001* (2013.01)

(58) Field of Classification Search
CPC . A61F 2/30965; A61F 2/3872; A61F 2/7812; A61F 2/38; A61F 2/3836
USPC ................................. 623/17.11, 14.12, 20.14
See application file for complete search history.

(56) References Cited

U.S. PATENT DOCUMENTS

| | | | |
|---|---|---|---|
| 4,502,161 A | 3/1985 | Wall | |
| 5,358,525 A | 10/1994 | Fox et al. | |
| 5,632,745 A | 5/1997 | Schwartz | |
| 5,755,797 A * | 5/1998 | Baumgartner | 623/17.16 |
| 5,934,653 A | 8/1999 | Rivin | |
| 6,132,468 A | 10/2000 | Mansmann | |
| 6,746,005 B1 | 6/2004 | Su et al. | |
| 2005/0043816 A1* | 2/2005 | Datta et al. | 623/23.61 |
| 2009/0036984 A1 | 2/2009 | Hagen et al. | |

OTHER PUBLICATIONS

Messner, K., The concept of a permanent synthetic meniscus prosthesis: a critical discussion after 5 years of experimental envestigations using Dacron and Teflon implants., Biomaterials, Mar. 1994, 243-50, 15-4.

Tienen et al, Prosthetic Replacement of the Medial Meniscus in Cadaveric Knees: Does the Prosthesis Mimic the Functional Behavior of the Native Meniscus?, Am J Sprts Med, 2004.

* cited by examiner

*Primary Examiner* — Christopher D Prone

(57) ABSTRACT

A cartilage replacement or repair prosthesis comprises a layer of streamlined elastomer elements, preferably in the form of spheres, supported in a matrix material so that the radially opposed surfaces of the spheres are positioned on opposite surfaces of the layer and make contact with the opposed surfaces of the femur and tibia and the forces exerted between these bones extend through the streamlined elements. The matrix material has a substantially lower resistance to deformation than the spheres to control the position of the spheres relative to one another without significantly restraining their load-responsive deformation under forces exerted between the femur and tibia. The layer, with its elastomeric inserts, is sufficiently thin and flexible to allow it to be rolled for arthroscopic insertion into a knee joint.

12 Claims, 2 Drawing Sheets

PROSTHESIS FOR REPLACEMENT OF CARTILAGE

CROSS-REFERENCE TO RELATED APPLICATIONS

This application claims priority of U.S. Provisional Patent Application Ser. No. 61/242,152 filed Sep. 14, 2009, which is incorporated herein by reference.

FIELD OF THE INVENTION

This invention relates to bone joint prostheses for replacing or repairing damaged cartilage and more particularly to prostheses employing streamlined elastomeric elements for transmitting the compressive and shear forces exerted on knees and other joints.

BACKGROUND OF THE INVENTION

Knee joints, which connect the tibia and the femur, are effected through a layer of cartilage, the meniscus, which has a very low friction coefficient but is sensitive to local pressure concentrations. The meniscus is subjected, in use, to compressive and sliding forces. The failure mode of the knee joint is usually wear of the meniscus due to sliding under high-contact forces and/or cracking of the cartilage caused mainly by local pressure concentrations while sliding. Injury and disease can lead to the need to remove the entire meniscus, or portions thereof.

The prior art has suggested a variety of constructions for cartilage replacement in the knee joint. U.S. Pat. No. 5,358,525 discloses a prosthesis consisting of a pad of pliable and compliant shock absorbing material supporting a plurality of small ball bearings which are capable of shifting positions within the interior of the replacement pad as varying loads are applied. U.S. Pat. No. 4,502,161 discloses a meniscus prosthetic comprising a resilient material such as silicone rubber or Teflon reinforced with a mesh of stainless steel or nylon strands.

These and other meniscus prosthetics have not experienced wide adoption in knee joint repair, and most knee joint repairs involve complete removal of the joint and replacement with an artificial joint formed between two bone replacement sections which are adapted to merge with the natural bone remaining after the joint removal.

SUMMARY OF THE INVENTION

The present invention is accordingly directed toward a meniscus prosthetic which successfully mirrors the function of the original cartilage pad or damaged portions of the pad, ideally to avoid the need for surgical removal of the entire knee joint. In a preferred embodiment of the invention, which will subsequently be disclosed in detail, the prosthesis comprises a pad formed by a single layer of streamlined elastomeric resilient elements disposed in a relatively compliant matrix. Compression forces and deformations in the functioning joint between the contact surfaces of femur and tibia bones are accommodated by nonlinear compression deformation of elastomeric streamlined, preferably spherical, elements which can be repeatedly compressed without failure up to 50%. Limited lateral relative displacements between femur and tibia in the functioning joint according to the instant invention are accommodated by limited rolling of the spherical compressed spherical elements, thus eliminating undesirable friction and wear of the prosthetic meniscus.

Rivin U.S. Pat. No. 5,358,525 discloses the structure and function of a flexible connector for transmitting forces between a pair of opposed rigid surfaces employing "streamlined" resilient elements defined as comprising spheres, cylinders, ellipsoids, etc. which are capable of undergoing a rolling motion when subjected to shearing forces between the two load transmitting end pieces and are similarly capable of resiliently absorbing straight compressive forces. The streamlined elements exhibit progressively nonlinear deformation characteristics under loading. As the streamlined elements are compressed, they progressively enlarge their bearing areas in contact with the rigid force transmitting elements. They may thus be designed so as to have a low relative compression when subjected to low forces and higher relative compression as the forces increase.

In the present invention the members of a singular layer of streamlined compressive elements are maintained in position relative to one another during distortion as a result of their being subjected to compressive and shearing forces, by a compliant matrix which allows limited displacement of the elements relative to one another. The matrix is subjected to some of the forces imposed between the load transmitting elements but is designed so as to not significantly restrain the load responsive deformation or the relative displacement of the elements under loading.

In the preferred embodiment of the invention, which will subsequently be disclosed in detail, the matrix takes the form of a relatively high flexibility elastomeric material such as foam in which the streamlined elements are embedded. In an alternative embodiment of the invention the matrix takes the form of a membrane or thin fibers extending between each resilient element and the neighboring resilient elements in the layer. In still another embodiment of the invention the streamlined elements are connected by the fibers and both are embedded in a matrix of soft elastomeric material, preferably in foamed condition.

The ratio of resistance to deformations between the streamlined elements and the supporting matrix is preferably 6 to 1 or greater.

The prosthetic layer, for use in the knee, may have a thickness ranging from 0.25 mm to 4 mm, and preferably has a thickness of about 1 mm.

BRIEF DESCRIPTION OF THE DRAWINGS

The following detailed description of a preferred embodiment of the invention makes reference to the accompanying drawings in which.

DETAILED DESCRIPTION OF THE PREFERRED EMBODIMENTS OF THE INVENTION

While the preferred embodiment of the invention involves use for the replacement of all or part of the cartilage layer of a knee joint, this and other embodiments of the invention can be employed in any of a similar mammalian joint such as a shoulder joint, hip joint, etc., which employs a cartilage sandwiched between two articulating bones which impose both compressive and shear forces on the associated soft tissue.

Figure 1:
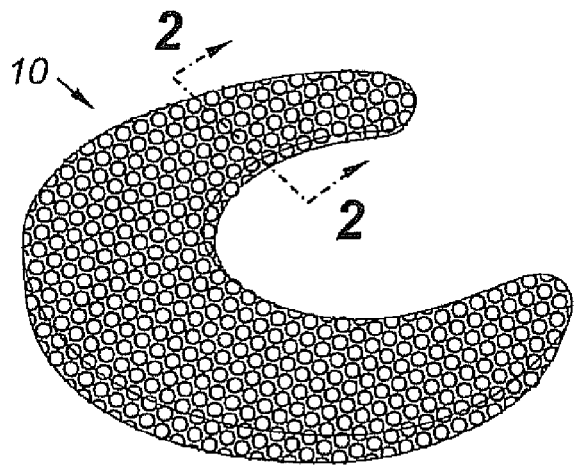
FIG. 1 is a perspective view of a prosthesis for replacing a segment of damaged cartilage in a joint, such as a knee joint, to replace a lateral meniscus or damaged sections of the meniscus.
Figure 2:
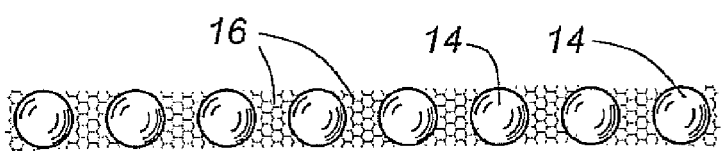
FIG. 2 is a cross-sectional view through the meniscus prosthesis using foam matrix of FIG. 1 taken along lines 2-2 of FIG. 1.

FIG. 1 is a perspective view of a prosthesis to replace a meniscus of a knee, not yet inserted between the contact surfaces of femur and tibia bones. The knee employs two similar meniscuses and a prosthesis for a lateral meniscus. The prosthesis comprises a pad generally indicated at 10. The pad, illustrated in cross section in FIG. 2, comprises a singular layer of elements 14, in this case compressible spherical elements having diameters which substantially equal the thickness of the pad 10 so that diametrically opposed points on each of the spherical elements 14 are disposed on opposite sides of the pad 10. In another embodiment shown in FIG. 6, the spherical elements 14 may have different diameters, and consequently the thickness of that pad 12 would not be constant, while still, diametrically opposed points on each of the spherical elements 14 are disposed on opposite sides of the pad 10.

The spherical elements 14 are the preferred form of the class of streamlined elements such as radially loaded cylinders, ellipsoids, toruses, etc., which are capable of rolling under a shearing load, even while compressed. These streamlined elements are formed of a relatively stiff elastomer material which is capable of resiliently compressing under normal loading and display a progressively nonlinear deformation characteristic. That is, as the streamlined elements are compressed they progressively enlarge their areas in contact with the rigid force transmitting elements and exhibit an increased resistance to deformation by those forces.

The thickness of the pad 10 and thus the diameter of the streamlined elements 14 may be on the order of 1 mm and could range from about 0.25 mm to about 4 mm.

The streamlined elements 14 may be embedded in an elastomeric matrix 16, such as foam, which acts to retain the spheres 14 in relative position with respect to one another while accommodating the forces imposed on the knee. The matrix 16 may be of the same composition as the material of the streamlined elements 14, but should be substantially softer than the streamlined elements 14. Preferably the resistance to deformation of the matrix 16 will not exceed about one sixth of the resistance to deformation of the streamlined elements 14. Given that, the matrix material can adequately control the position of the elements 14 under loading without significantly restraining the load-responsive deformation of the elements 14, both in compression and in directions transverse to the loading axis as a result of the shearing motion between the femur and tibia or other bones, depending upon the joint.

Figure 3:
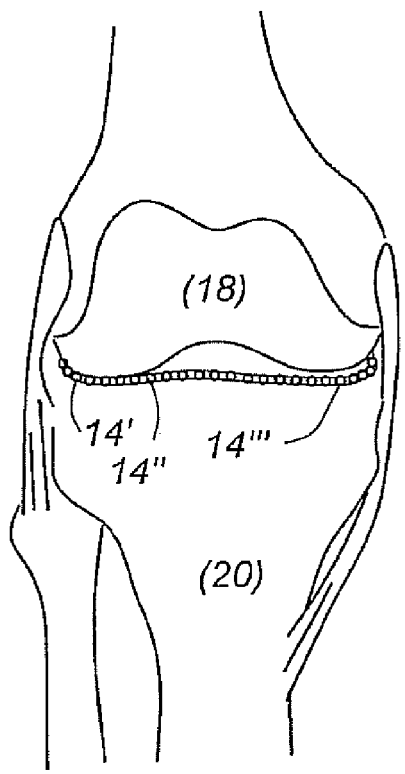
FIG. 3 is a view of a knee joint showing the prosthesis of FIG. 1 disposed between a femur and tibia of a knee joint.

FIG. 3 illustrates a cross section of a knee joint employing a prosthesis 10. The femur 18 and the tibia 20 have their opposed surfaces sandwiching the element 10 which has a shape corresponding but generally not conformal to their opposing (contact) areas.

Since the opposing contact surfaces of the femur and tibia bones to be connected by the joint are not conformal, high local contact pressures in relatively small contact areas are inevitable. These pressure areas are shifted during flexion of the knee. Accordingly, compression deformations of spherical elements 14 comprising pad 12 are not identical, with some elements, like 14' are compressed more than others (14") and some not compressed at all (14''') during functioning of the proposed prosthetic joint. The maximum contact load for a moving person weighing 70 kg may be ~1750 N and the average contact pressure may be as high as 5 MPa and the peak pressure double that, or ~10 MPa. In a human knee joint with cartilage, the compression deformations under full load are on the order of 0.3 mm and the elastomeric streamlined elements 14 are preferably designed to provide a similar deformation under full load. The streamlined elements 14 are formed to provide a deformation similar to that of the natural meniscus under full loading of the knee.

Figure 4:
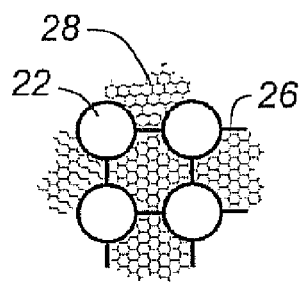
FIG. 4 is a perspective view of a portion of an embodiment of the invention employing a plurality of spherical streamlined elements secured in position relative to one another by fibers extending between neighboring elements, with the elements and the fibers embedded within a low stiffness elastomeric matrix, preferably in foamed condition.
Figure 5:
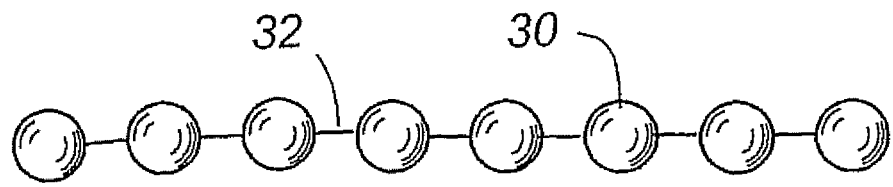
FIG. 5 is a cross section through still another alternative embodiment in which there is no matrix but the pad simply consists of elements connected by fibers.

FIGS. 4 and 5 illustrate a pad in which a plurality of streamlined spheres 22 are arranged in an alternative form of the prosthetic pad of the present invention. The spheres 22 are joined to one another by fibrous filaments 26 which extend between each of the spherical elements 22 and each of its neighboring elements. The spheres 22 and their fibrous connectors 26 are preferably embedded within an elastomeric matrix 28, of a similar material to the material 16 employed with the embodiment of FIG. 1. Both the matrix 28 and the fibers 26 act to retain the spheres 22 in their proper relative positions.

FIG. 5 is a cross section through still another alternative embodiment in which there is no matrix but the pad simply consists of spheres 30 connected by fibers 32 arranged in the same formation as the pad of FIG. 1.

Figure 6:
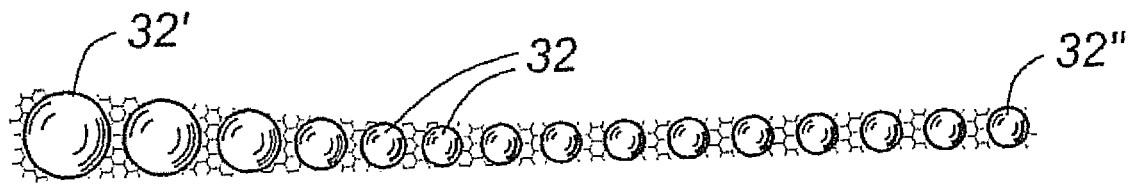
FIG. 6 is a cross-sectional view through another embodiment of the pad of the present invention formed by a plurality of streamlined spherical elements having different diameters.

FIG. 6 is a cross sectional view of an embodiment of a pad comprising a plurality of spheres 32 of varying size ranging from large diameters 32' to smaller spheres 32" to provide custom pads to accommodate different bone configurations.

Figure 7:
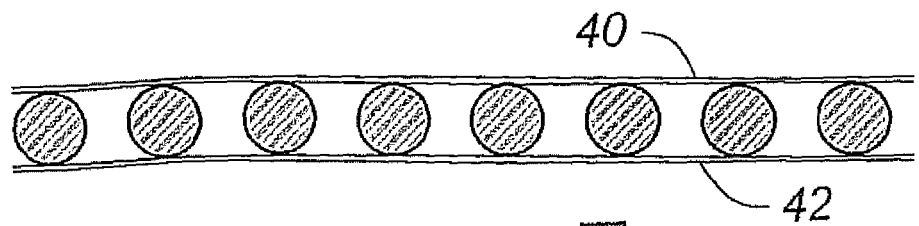
FIG. 7 is a sectional view through still another embodiment of the prosthesis pad formed by a plurality of spherical members joined by an upper or lower membrane.

FIG. 7 is a cross section through a prosthesis pad comprising a plurality of elastomeric spheres 30 joined and spaced relative to one another by one or more membranes 40, 42. Different embodiments of the invention may use any combination of constituents disclosed herein, including type of streamlined elements, elastomeric matrix, fibers and or membrane. For example, an alternative embodiment may use ellipsoids without a matrix but with fibers and one membrane. A different configuration may use differently sized cylinders joined with axial fibers in a matrix with one or no membrane, and so forth.

Figure 8:
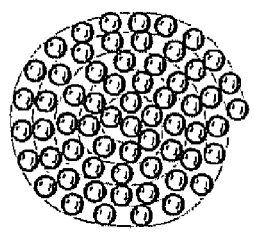
FIG. 8 is a sectional view through a pad formed in accordance with the invention wrapped into a compact spiral configuration for insertion into a knee joint during surgery.

As illustrated in FIG. 8, any of the pads of the present invention may be rolled into a compact cartridge for easy insertion into a knee joint or other region of the body as part of an arthroscopic procedure. The described prosthesis be attached to soft and/or hard (bones) tissues of the joint by one of known surgical techniques, e.g., by stapling or suturing. In the case of the knee joint, the periphery or other portions of the pad would preferably be fastened to one or more portions of the proximal tibia.

Figure 9:
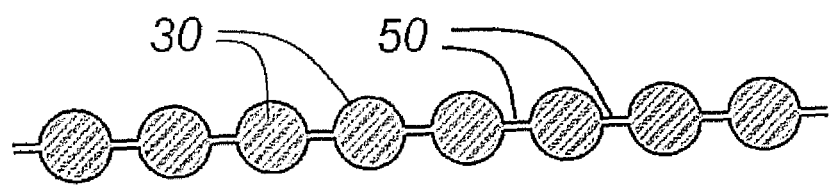
FIG. 9 a sectional view through a molded pad including a membrane interconnecting the elements around their equatorial centerlines.

The described prosthesis can be fabricated by known technologies of elastomeric parts production. A preferable technology is by molding the whole prosthesis simultaneously in a compression mold, leaving a membrane 50 interconnected the elements 30 near their equatorial centerlines, as shown in the cross section of FIG. 9. An advantage of this technique is that the same material may be used for the elements and the interconnecting membrane. Customizing the dimensions of the prosthesis can be achieved by cutting it with a scissors-like tool.

Having thus disclosed my invention, We claim:

1. A replacement prosthesis for all or part of the natural cartilage in a mammalian joint, comprising:
    a pad formed as a spaced array of a single layer of streamlined elastomeric elements with diametrically opposed points on each of the elements being disposed on opposed surfaces of the pad, the streamlined elastomeric elements having a first resistance to deformation; and
    a matrix contacting each of the streamlined elements at points between said diametrically opposed points so as to retain the streamlined elements in position relative to one another under the loading of the joint, the matrix having a second resistance to deformation which does not exceed about one sixth of the streamlined elements so that the matrix does not significantly influence the deformation characteristics of the streamlined elements under loading.

2. The prosthetic pad of claim 1 wherein the streamlined elements are spheres.

3. The prosthetic pad of claim 1 wherein the streamlined elements are spheres of the same diameter.

4. The prosthetic pad of claim 1 wherein the streamlined elements are spheres of different diameters.

5. The prosthesis pad of claim 4 wherein the matrix comprises filaments each having one of its ends joined to a streamlined element in the array and its opposite end joined to an adjoining streamlined element in the array.

6. The prosthesis pad of claim 5 wherein the volume between the filaments and the streamlined elements is filled with an elastomeric material having a resistance to deformation not exceeding about one sixth of the resistance to deformation of the streamlined elements.

7. The prosthesis pad of claim 4 wherein the matrix comprises a membrane whose thickness is significantly thinner than diameters of the streamlined elements in the array and is attached to each streamlined element at or close to its diametral cross section, thus creating an integral pad.

8. The prosthetic pad of claim 1 wherein the streamlined elements are chosen from the class consisting of spheres or radial-loaded cylinders.

9. The prosthetic pad of claim 1 wherein the matrix includes an elastomeric material embedding the streamlined elements and filling the volume of the pad between the streamlined elements.

10. The prosthetic pad of claim 1 wherein the pad is sandwiched between the surfaces of a human femur and tibia.

11. The replacement prosthesis of claim 1 wherein the array is in the form of a planar pad having a thickness in the range of 0.25 millimeters-4 millimeters.

12. A prosthesis pad for replacement of cartilage in a human joint, comprising:
    a substantially planar pad having a thickness in the range of 0.25-4 millimeters, the pad comprising an array formed of a single layer of spherical elastomeric elements having a first resistance to deformation, the spherical elements each having diameters equal to the thickness of the pad in the area of placement of said spherical element, and having diametrically opposed points on their surfaces on the opposite surfaces of the pad, and a matrix whose resistance to deformation does not exceed about one sixth of the first resistance to deformation disposed in contact with the surfaces of each of the spheres so as to fill the volume of the pad not occupied by the spheres.

* * * * *